United States Patent [19]

Scherrer

[11] Patent Number: 5,472,848
[45] Date of Patent: Dec. 5, 1995

[54] METHODS TO AID IN THE DIAGNOSIS OF MULTIPLE SCLEROSIS

[75] Inventor: Klaus Scherrer, Paris, France

[73] Assignee: Pro Soma S.A.R.L., Paris, France

[21] Appl. No.: 237,966

[22] Filed: May 2, 1994

Related U.S. Application Data

[63] Continuation of Ser. No. 60,464, May 12, 1993, abandoned, which is a continuation of Ser. No. 889,219, May 27, 1992, abandoned.

[30] Foreign Application Priority Data

Jun. 21, 1991 [EP] European Pat. Off. .............. 91401443

[51] Int. Cl.⁶ .................. G02N 33/53; G01N 33/543; G01N 33/551; C12Q 1/00
[52] U.S. Cl. .................. 435/7.92; 436/518; 436/524; 436/811
[58] Field of Search .................. 435/7.1, 7.92, 435/7.93, 7.94, 7.95, 975; 436/506, 518, 525, 530, 808, 811, 524

[56] References Cited

U.S. PATENT DOCUMENTS

| | | | |
|---|---|---|---|
| 4,313,734 | 2/1982 | Leuvering et al. | 436/525 |
| 4,533,496 | 8/1985 | Lewis, Jr. et al. | 435/68 |
| 4,859,612 | 8/1989 | Cole et al. | 436/523 |
| 5,059,521 | 10/1991 | Scherrer et al. | 435/7.1 |

FOREIGN PATENT DOCUMENTS

| | | |
|---|---|---|
| 0219368 | 4/1987 | European Pat. Off. . |
| 0345750 | 12/1989 | European Pat. Off. . |

OTHER PUBLICATIONS

Arribas et al, "Autoantibodies against the Multicatalytic Protinase in Patients with Systemic Lupus Erythematosus", J. Exp. Med., 173: 423–427 (Feb. 1991).
Ivan M. Roitt, Essential Immunology, 5th Edition (Blackwell Scientific Publications, Oxford, 1984) pp. 151–153.
Smith et al Ann. Clin. Biochem vol. 18 (1981) 253–274.
Research Reagent News, vol. 1, Jan. 1, 1990, "Anti–prosomal Mouse monoclonal antibodies," pp. 1–4, published by Organon Teknika, N.V.

Primary Examiner—Toni R. Scheiner
Assistant Examiner—Patricia A. Duffy
Attorney, Agent, or Firm—Mary E. Gormley

[57] ABSTRACT

Disclosed are methods and kits useful in the differential diagnosis of multiple sclerosis. The method involves the use of an immunochemical reagent containing one or more prosomal antigens. Such a method typically involves: obtaining serum from a patient suspected of suffering from multiple sclerosis; contacting the immunochemical agent with the serum; and detecting the presence of immune complexes formed between the prosomal antigen and any antibodies reactive therewith present in the serum.

6 Claims, 1 Drawing Sheet

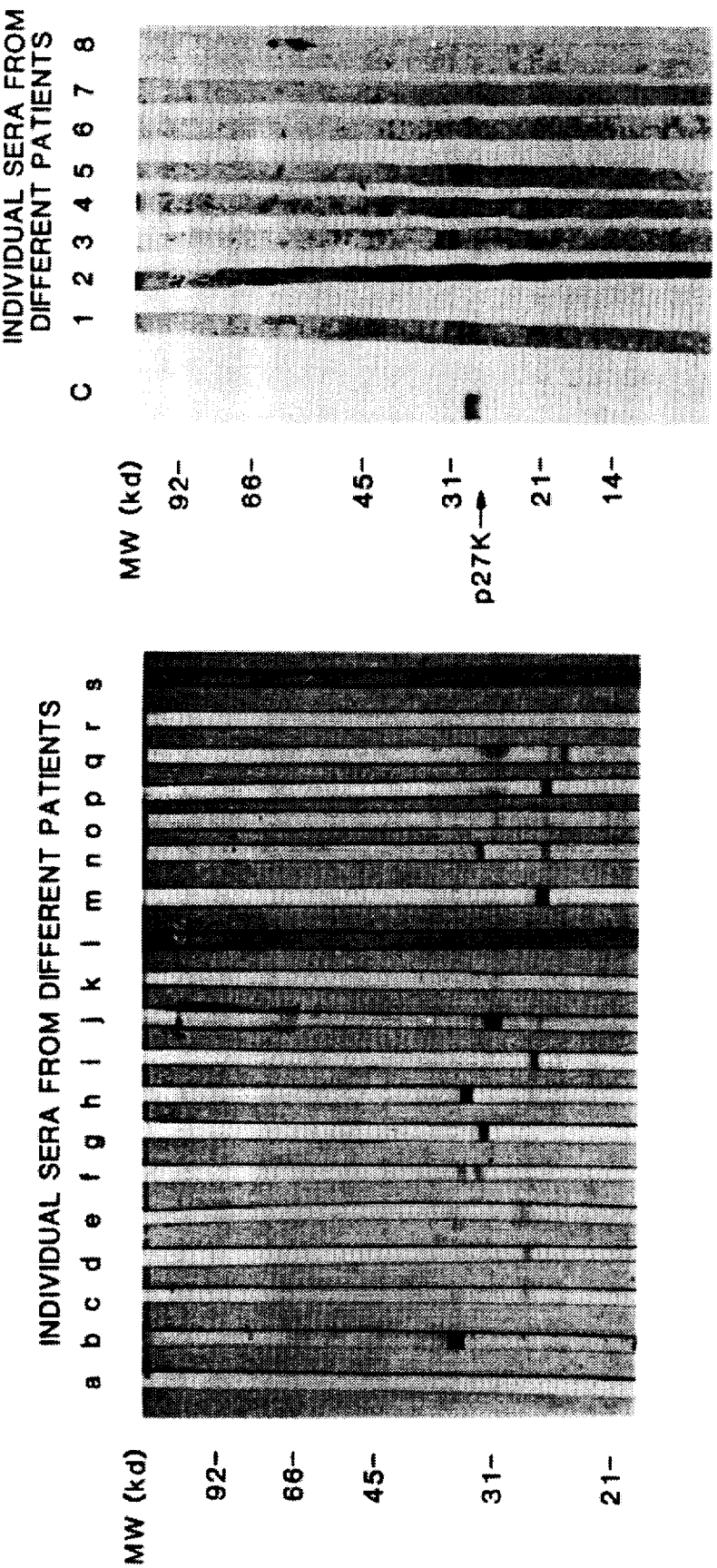

5,472,848

METHODS TO AID IN THE DIAGNOSIS OF MULTIPLE SCLEROSIS

This is a continuation of application Ser. No. 08/060,464 filed May 12, 1993, now abandoned, which is a continuation of application Ser. No. 07/889,219, filed May 27, 1992, now abandoned.

BACKGROUND OF THE INVENTION

1. Field

This invention relates to a method and apparatus useful in the differential diagnosis of multiple sclerosis.

2. State Of the Art

Multiple sclerosis ("MS") is a disease which usually presents itself in the form of recurrent attacks of focal or multifocal neurologic dysfunction. Its symptoms are multifaceted and indefinite and include impaired vision, nystagmus, an inability to speak clearly, a decreased perception of vibration and position sense, intention tremor, muscular incoordination, limb weakness or paralysis, spasticity, and bladder problems. *Harrison's Principles of Internal Medicine*, p. 1995–2000 (11th ed. 1987). Unfortunately, no effective treatment of MS is known.

In order to establish a definite diagnosis of MS, at least two episodes of neurological deficit must occur along with objective clinical signs of lesions at more than one site within the central nervous system. One problem with such a diagnostic method is that a period of ten to twenty years may pass between episodes of neurological deficit. Id.

Another problem is that the symptoms of MS are so indefinite that it may be confused with several other conditions. It is therefore important during the differential diagnosis of the patient to exclude conditions having similar symptoms which can be effectively treated. For example a patient may be suffering from side-effects of various prescription drugs (e.g. phenytoin which can cause nystagmus, vertigo and muscle weakness), pernicious anemia, or various infections. Usually such conditions can be effectively treated.

A need therefore exists for a relatively simple device useful in the determination of whether or not someone might be suffering from MS.

SUMMARY OF THE INVENTION

Surprisingly, it has been found that a great number of MS patients (more than ninety percent of those tested in one test series) have antibodies circulating in their blood stream to prosomes, while very few of those not suffering with the disease had such antibodies (<3% of those tested).

The invention thus includes a method of using a "prosomal antigen" (e.g. a prosome, prosomal protein, fragment, or derivative thereof), no matter what the source, in the differential diagnosis of multiple sclerosis. Typically such a method will utilize an immunochemical reagent containing one or more of the prosomal antigens.

Such a method would typically involve: obtaining serum from a patient suspected of suffering from multiple sclerosis; contacting the described immunochemical agent with the serum; and detecting the presence of immune complexes formed between the prosomal antigen and any antibodies reactive therewith present in the serum.

BRIEF DESCRIPTION OF THE FIGURES

FIG. 1 is a photographic reproduction of the immunoreaction between sera of 19 multiple sclerosis patients and purified prosomes from HeLa cells.

FIG. 2 is a photographic reproduction of the immunoreaction between sera of 8 other multiple sclerosis patients and purified prosomes from HeLa-cells.

DESCRIPTION OF THE PREFERRED EMBODIMENTS

I. Prosomal Antigens

"Prosomal antigen" as used herein, means a prosome, prosomal protein, fragment, or derivative thereof, no matter what the source, for example from cells or those produced by genetic engineering techniques.

Prosomes are a kind of ubiquitous ribonucleoprotein particle of variable composition. They are composed of about 95% or more protein ("prosomal protein") and about 5% or less RNA ("pRNA"). Prosomes represent a morphologically and biophysically uniform class of 12-nm-wide raspberry or cylindrically shaped particles which vary in individual protein and RNA composition. At least 25 different prosomal proteins have been observed. Prosomes have been found in the cells of all species thus far tested. However, for the present invention, prosomes (and prosomal antigens) of human origin are preferred.

Prosomes are isolatable. The postmitochondrial supernatant of normal cells are fractionated by differential centrifugation in order to produce polyribosomes, pellets of postpolyribosomal particles, and the cytosol fraction. Prosomes have been obtained from the postpolyribosomal pellet by sucrose gradient sedimentation in high-ionic strength buffers. See, e.g. Martins de Sa et al, "Prosomes: ubiquity and inter-species structural variation," *J. Molec. Biol.*, 187: 151–158 (1986); Schmid et al, "The prosome an ubiquitous morphologically distinct RNP particle associated with repressed mRNPs and containing ScRNA and a characteristic set of proteins", *EMBO J.* 3: 29–34 (1984) Under these conditions, the prosome sediments as a sharp peak with a sedimentation value of about 19S.

Prosomal proteins which help to make up the prosome have also been characterized. See, e.g. Schmid et al, supra. Prosomal proteins p27K and p33K—corresponding to proteins having an approximate molecular weight of 27 and 33 kilodaltons respectively—have been sequenced and are identified in co-owned, International Application No. PCT/EP91/01945 (International Publication No. WO 92/07269 published on 30 Apr., 1992) under SEQ ID NO:2 and SEQ ID NO:4 respectively. A "fragment" is typically an epitopic portion of a prosomal protein.

The preparation of peptides or fragments thereof for use with the invention may be by recombinant DNA methods or one of the known organic chemical methods for peptide synthesis.

Organic chemical methods are especially useful in the synthesis of smaller peptide fragments having the desired activity. Once the sequence of a fragment is known, the synthesis is rather straightforward for an ordinarily skilled peptide chemist. Organic chemical methods for peptide synthesis include coupling the required amino acids by means of a condensation reaction in either a homogenous phase or with the aid of a solid phase. The solid phase method is described in Merrifield, *J. Am. Chem. Society*, 85, 2149 (1963) and Wang, *J. Am. Chem. Soc.*, 95, 1328 (1974).

Recombinant DNA methods involve the preparation of the desired peptide or fragment by means of expressing a recombinant polynucleotide with a polynucleotide sequence which codes for one or more of the peptides in question in a suitable microorganism as host. Generally the process involves introducing into a cloning vehicle (e.g. a plasmid, phage DNA, or other DNA sequence able to replicate in a host cell) a DNA sequence; introducing said cloning vehicle into a suitable host cell; and culturing the host cell thus transformed. Typical host cells include bacteria such as *E. coli*, Pseudomonas, and *Bacillus subtilis*.

Once the peptides have been made, fragments useful in the invention can also be determined. Suitable immunochemically active peptide fragments can be found according by means of the method described in Patent Application WO 86/06487 to Geysen et al; Geysen et al, *Proc. Nat'l Acad. Sci.*, (81) 3998–4002, (1984); and Geysen et al, J. Immunol Meth., (102) 259–274 (1987) based on the "pepscan" method. In this method a series of overlapping peptides corresponding with partial sequences of the complete peptide under consideration are synthesized and their reactivity with the antibodies is investigated.

Furthermore functional derivatives of the peptides may also be used. Such functional derivatives include acid addition salts (such as hyurochloric, hydrobromic, fumaric, phosphoric, ascorbic, tartaric, citric, lactic, maleic, palmitic, and other well-known acids) of the peptides; amides of the peptides and especially the C-terminal amides; esters and especially C-terminal esters; and N-acyl derivatives, especially N-terminal acyl derivatives and in particular N-acetyl derivatives. All functional derivatives are considered "polypeptides", "peptides" and "peptide fragments" according to the invention.

Some prosomes, prosomal proteins, fragments and derivatives can be identified by their reactivity with certain antibodies commercially available from Organon Teknika, nv of Turnhout, Belgium. The commercially available monoclonal antibodies are those directed against prosomal proteins p23K, p25K, p27K, p29K (p28K, p33K), p30/33K, and p31K and the anti-p21K ("prosome-like particle"). These antibodies are more thoroughly described in *Research Reagent News*, (January 1990) available from Organon Teknika nv.

II. Antibodies

A. Subject's Antibodies

The sample to be tested must contain antibodies of the subject. Such samples include blood and blood fractions such as plasma or serum. A blood sample may be obtained from the subject to be tested, typically veinipuncture, and the red blood cells and clots are preferably removed. Antibodies may then be separated by any suitable technique.

B. Other antibodies

Other antibody substances for use in diagnostic kits and methods according to the invention are chosen according to the particular test to be used. For example, labelled antibodies directed against human IgG antibody are useful in certain embodiments of the invention for detecting any antibodies present in the sample taken from the subject which react with the prosomal antigen. Immunologically active antibody fragments of these antibodies are likewise useful. Antibodies against prosomal proteins are suited for binding prosomes to a solid support (preferably such antibodies would not be human or "humanized" antibodies). Such antibodies can be polyclonal or monoclonal antibodies.

Labelling substances typically used include various radioactive isotopes, fluorescent compounds, latex, enzymes, dye sols or metal compounds used as sol particles.

Labelled anti-human antibodies (labelled with, for example, peroxidase) are commercially available from, for example Miles Laboratories Ltd. of Slough, England.

Monoclonal antibodies produced against human antibodies can also be produced by biologically pure cell lines of immortalized antibody-producing cells. Immortalized antibody producing cells can be obtained according to any of the various methods which are known in the art, and generally include the steps: 1) inducing suitable cells such as lymphocytes to produce specific antibodies, 2) immortalizing those cells, and 3) selecting clones out of these cells which produce antibodies of the desired specificity and affinity. For example, one method would be that of Kohler and Millstein, *Nature*, vol. 256, 495–497 (1975). This method comprises immunizing mice with human antibody, isolating spleen cells and fusing these with mouse myeloma cells to obtain hybridomas. Of course animals other than mice could be used as well.

Other methods for producing antibodies are disclosed in U.S. Pat. No. 4,816,397 (methods for producing recombinant antibodies) and U.S. Pat. No. 4,816,567 (recombinant chimeric antibodies).

II. Diagnostic Methods

Prosomal antigens displaying antigenicity with the MS antibody may be used in methods and kits designed to detect the presence of those antibodies in humans.

A prosomal antigen displaying the desired immunogenic activity produced by, for example, hosts transformed by recombinant DNA molecules of the invention, can be used in immunological reagents or immunological diagnostic test kits.

As used herein an "immunochemical reagent" means that prosomal antigen or antigens have been bound, directly or indirectly, to a suitable support. Supports typically used include the inner wall of a microtest well or a cuvette, a tube or capillary, a membrane filter, test strip, or the surface of a particle such as a latex particle, bead, erythrocyte, dye sol, metal sol or metal compound as sol particle.

In one method of detecting the presence of antibodies directed against the proteins in a test fluid (e.g. serum of a human thought to be suffering from multiple sclerosis), an immunochemical reagent of the invention is brought into contact with the test fluid. After which the presence of immune complexes formed between the peptide and antibodies in the test fluid is measured for the presence of an immunochemical reaction. The immunochemical reaction is preferably a sandwich reaction (using either labelled peptide or labelled antihuman antibody), an agglutination reaction (using also sols), a competition reaction, or an inhibition reaction.

Immunological diagnostic test kits include radio-immunoassay or enzyme immunoactivity assay ("EIA") as described in U.S. Pat. No. Re. 32,696 to Schuurs et al, and metal sol particle immunoassays ("SPIA") such as is described in U.S. Pat. No. 4,313,734 to Leuvering, the contents of which are incorporated by this reference. Aqueous sol dispersions of a metal, metal compound or polymer nuclei coated with a metal or metal compound are used in "SPIA" test kits.

In one preferred immunoassay for detecting the MS antibodies, a predetermined quantity of prosomal antigen is adsorbed on a solid phase, protein binding surface. The test sample to be assayed for antibodies (e.g. a patient's serum) is then contacted to the surface having prosomal antigen bound thereto, and antibodies in the test sample bind to the immobilized antigen. Radioactive or enzyme-labeled immunoglobulin probes (e.g. antibodies or antibody fragments which only react with human IgG) are then contacted to the surface and bind to the immobilized antibodies. The amount of labelled probe bound to the solid support can be determined and is indicative of the presence of antibody in the test sample.

In one type of radioimmunoassay, antibodies against prosomal antigen (e.g. those described in U.S. Pat. No. 5,059,521 to Scherrer et al.) are attached to a solid phase, for example the inside of a test tube. Prosomal antigen is then added to the tube so as to bind with these antibodies. To the tube coated with the thus formed antigen-antibody complex is added a sample of the patient's serum, together with a known amount of antibodies against prosomal antigen labelled with a radioactive isotope such as radioactive iodine. Any antibody directed against the prosomal antigen from the patient's serum will compete with the labelled antibodies for the free binding sites on the antigen-antibody complex. Once the serum has been allowed to interact, the excess liquid is removed, the test tube washed, and the amount of radioactivity measured. A positive result, i.e. that the patient's serum contains the antibodies is indicated by a relatively low radioactivity count.

In one type of EIA test, a microtitre plate is coated with the prosomal antigen and to this is added a Sample of patient's serum. After a period of incubation permitting interaction of any antibody with the antigen, the plate is washed and a preparation of anti-human antibodies, e.g. raised in a laboratory animal, and which are linked to an enzyme label is added, incubated to allow reaction to take place, and the plate is then washed again. Thereafter enzyme substrate is added to the microtitre plate and incubated for a period of time to allow the enzyme to work on the substrate, and the adsorbance of the final preparation is measured. A large change in adsorbance indicates a positive result.

Alternatively, prosomal proteins can be extracted, and then fractionated in a matrix. The separated proteins are immobilized by transfer to a membrane and reacted with antibody from the subject. The membrane is then preferably washed. Labelled (directly or indirectly) anti-human antibodies are then reacted to determine if binding between the subject's antibodies and the prosomal protein occurred.

The diagnostic test kits of the invention may also contain auxiliaries such as buffers, standards (negatives and positives), and materials (e.g. chemicals) necessary for the detection of the label. If the label is an enzyme, substrate for this enzyme may be included in the test kit; if the label is a sol particle of a dye, metal, or metal compound, the test kit may contain chemicals to dissolve the label bound to a solid support, in order to enhance the detection.

The invention is further explained by reference to the following illustrative example.

EXAMPLE

Prosomes from HeLa cells were obtained according to the procedure set forth in Example 1 of U.S. Pat. No. 5,059,521 to Scherrer et al, published on 22 Oct., 1991. These prosomes were further purified by passing them over a 0.5% sarcosyl gradient.

Sera was obtained from 27 patients previously diagnosed as, or suspected of, suffering from multiple sclerosis ("Group A"). Sera of 35 persons, none of whom were believed to be suffering from multiple sclerosis, were also tested as negative controls ("Group B"). Purified prosomes from HeLa cells were loaded onto a 13% polyacrylamide SDS-gel (SDS-PAGE). After electrophoresis, the prosomal proteins were blotted onto a nitrocellulose membrane (Bio-Rad). Strips of the membrane were cut and saturated with 5% skimmed milk in PBS for one hour. They were then incubated with the different sera for two hours at room temperature (dilution 1:1000). After 3 washes in saturated buffer, the reacting antibodies of these sera were secondarily detected with an anti-human IgG antibody conjugated with peroxidase (Miles Labs. Ltd., Slough, England) by incubating for two hours at room temperature and revealed by $H_2O_2$-chloronapthol. The negative control was replaced by the dilution buffer.

25 of the 27 sera from Group A (93%) displayed prosome positive reactions in the molecular weight range of 25 to 35 kilodaltons. Most of this sera reacted positively with a single or double protein ban but at different molecular weight ranges (i.e. 25Kd, 27Kd, 31Kd and 33Kd approximately). The results are shown in FIGS. 1 and 2.

One of the sera from Group B displayed prosome positive reactions.

The use of specific examples and embodiments should not be construed as limitations to the scope of the invention which is defined by the appended claims.

What is claimed is:

1. A method useful in the differential diagnosis of multiple sclerosis comprising:
    a) contacting a sample containing antibodies of a subject with an immunochemical reagent comprising prosomal antigen; and
    b) detecting the presence of immune complexes formed between the prosomal antigen and any antibodies reactive therewith present in the sample.

2. The method of claim 1 wherein said prosomal antigen is a prosome derived from human cells.

3. The method of claim 1 wherein said prosomal antigen is prosomal protein selected from the group of prosomal proteins consisting of a molecular weight of approximately 25, 27, 31, and 33 kilodaltons.

4. A method to aid in the diagnosis of multiple sclerosis comprising the following steps:
    (a) binding prosomal antigen to the surface of the solid carrier;
    (b) contacting said bound prosomal antigen with a test sample from a subject;
    (c) allowing sufficient time for an immunological complex between the prosomal antigen and any autoantibodies that specifically bind to prosomal antigen present in the test sample to take place, thus forming a first solid phase and first liquid phase;
    (d) separating the first liquid and first solid phases;
    (e) contacting said first solid phase with an anti-human immunoglobulin labelled with metal sol that specifically binds to said autoantibodies in said immunological complex, thereby forming a second solid and second liquid phase;
    (f) separating the second solid and second liquid phases;
    (g) determining the presence of said autoantibodies by detecting the presence or the amount of said metal sol label on the second solid phase, wherein the presence of autoantibodies to prosomal antigens indicates multiple sclerosis in a subject.

5. The diagnostic method of claim 4, wherein said prosomal antigen is a prosome derived from human cells.

6. The diagnostic method of claim 4, wherein said prosomal antigen is a prosomal protein selected from the group consisting of prosomal proteins having a molecular weight of approximately 25, 27, 31 and 33 kilodaltons.

* * * * *